(12) United States Patent
Powers

(10) Patent No.: US 7,899,529 B2
(45) Date of Patent: Mar. 1, 2011

(54) APPARATUS AND METHOD FOR PACKAGING A CAPACITOR

(75) Inventor: Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1044 days.

(21) Appl. No.: 10/574,343

(22) PCT Filed: Sep. 21, 2004

(86) PCT No.: PCT/IB2004/051812
§ 371 (c)(1), (2), (4) Date: Mar. 30, 2006

(87) PCT Pub. No.: WO2005/034154
PCT Pub. Date: Apr. 14, 2005

(65) Prior Publication Data
US 2007/0010134 A1 Jan. 11, 2007

Related U.S. Application Data
(60) Provisional application No. 60/509,018, filed on Oct. 6, 2003.

(51) Int. Cl.
*A61N 1/39* (2006.01)
(52) U.S. Cl. .......................................................... 607/5
(58) Field of Classification Search ................ 607/5, 607/10; 439/620.09–620.14
See application file for complete search history.

(56) References Cited
U.S. PATENT DOCUMENTS

| | | | | |
|---|---|---|---|---|
| 2,704,181 A | | 3/1955 | Henderson et al. | |
| 4,546,300 A | * | 10/1985 | Shaikh | 318/786 |
| 4,754,361 A | | 6/1988 | Venturini | |
| 5,142,103 A | | 8/1992 | Stine | |
| 5,645,571 A | * | 7/1997 | Olson et al. | 607/5 |
| 5,741,313 A | | 4/1998 | Davis et al. | |
| 5,749,904 A | | 5/1998 | Gliner et al. | |
| 6,141,205 A | | 10/2000 | Nutzman et al. | |
| 6,275,729 B1 | | 8/2001 | O'Phelan et al. | |
| 6,327,133 B1 | | 12/2001 | Bauer | |
| 6,373,127 B1 | | 4/2002 | Baudouin et al. | |
| 6,522,525 B1 | | 2/2003 | O'Phelan et al. | |
| 6,535,096 B1 | * | 3/2003 | Rapoport et al. | 336/96 |
| 2002/0034062 A1 | | 3/2002 | O'Phelan et al. | |
| 2002/0085334 A1 | | 7/2002 | Figueroa et al. | |

FOREIGN PATENT DOCUMENTS

| | | | |
|---|---|---|---|
| DE | 3507092 A1 | | 8/1986 |
| GB | 1368057 | * | 9/1974 |
| GB | 1368057 A | | 9/1974 |
| JP | 9500309 T | | 1/1997 |
| JP | 2001210548 A | | 8/2001 |

* cited by examiner

Primary Examiner—Scott M Getzow
Assistant Examiner—Amanda Patton
(74) Attorney, Agent, or Firm—W. Brinton Yorks, Jr.

(57) ABSTRACT

An electronic device includes a housing (20) having a first interior region (26) and a second interior region (28). The second interior region (28) is sized to receive an electronic interface (18). The device also includes a wound capacitor core (14) adapted for electrical communication with the second interior region (28), and a capacitor potting material (38) disposed in contact with the first interior region (26) and the wound capacitor core (14).

15 Claims, 4 Drawing Sheets

APPARATUS AND METHOD FOR PACKAGING A CAPACITOR

CROSS REFERENCE TO RELATED APPLICATION

This application claims the benefit of U.S. provisional application Ser. No. 60/509,018 filed Oct. 6, 2003, which is incorporated herein.

Aspects of this invention relate generally to capacitors, and more particularly to an apparatus and method for packaging an energy storage capacitor, and to an electronic device, and an electronic instrument having an energy storage capacitor.

Energy storage capacitors that include wound capacitor cores, such as metallized film cores, are typically manufactured as discrete components—the wound capacitor cores are surrounded by potting material such as oil or epoxy, and encapsulated using metal or plastic cans, to form complete capacitor assemblies. The complete capacitor assemblies are then assembled into an electronic device, such as a portable external defibrillator.

FIG. 1 illustrates two views of an electronic device, an external defibrillator, comprising a complete capacitor assembly 2 with protective metal or plastic can 3. A completed capacitor assembly 2 is generally secured into a redundant housing 4, such as molded enclosures or cradles, within electronic instruments such as external defibrillators. In addition, adhesives, pads, support ribs 6 or other structures, fasteners, and/or a combination thereof, must generally be used to further secure capacitor assemblies into the electronic instruments. Because capacitor assemblies account for much of the volume of many electronic instruments, especially those that require a large store of high voltage energy, the electronic instruments may require large voids around the support members that cause the instrument to be volumetrically inefficient. Such voids may compromise the structural strength of the capacitor and possibly the instrument itself.

In addition, the assembly of the electronic instrument with a pre-manufactured capacitor adds cost to the instrument. The prior art assembly process is also a possible source of defects.

There is therefore a need for an electronic instrument, an electronic device, and an apparatus and method for packaging an energy storage capacitor for use with an electronic instrument, with, among other things, increased volumetric efficiency, more reliable assembly, and lower cost.

According to one aspect of the present invention, an apparatus for packaging an energy storage capacitor is adapted for use with an electronic instrument. The energy storage capacitor has a wound core, adapted for electrical connection to capacitor interface electronics associated with the electronic instrument. The apparatus includes an interior housing surface having a first region and a second region. The first region is sized to receive the wound core and a potting material, and has a cavity defined by a side surface, a closed first end, and an at least partially open second end. The second region is sized to receive the capacitor interface electronics. An exterior housing surface is arrangeable to at least in part surround the interior housing surface. When the wound core is disposed in the first region, the wound core is arranged in such a manner that a void for receiving the potting material is positioned between the wound core and the side surface, and a conductive path adapted to electrically connect the wound core and the capacitor interface electronics is arrangeable between the wound core and the second region.

According to another aspect of the present invention, a method for packaging an energy storage capacitor is provided. The energy storage capacitor has a wound core adapted for communication with capacitor interface electronics associated with an electronic instrument. The method includes: providing an interior housing surface having a first region and a second region, the first region having a cavity defined by a side surface, a closed first end, and an at least partially open second end, the second region sized to receive the capacitor interface electronics; arranging the wound core in the first region in such a manner that a void for receiving the potting material is positioned between the wound core and the side surface, and the wound core is positioned for communication with the capacitor interface electronics, when the capacitor interface electronics are disposed in the second region; and depositing the potting material into the void.

According to a further aspect of the present invention, an electronic instrument includes a housing, and the housing includes a first interior region and a second interior region. The first interior region defines a first cavity and has a configuration defined by a side surface, a closed first end an at least partially open second end. The second interior region defines a second cavity. The electronic instrument also includes a wound capacitor core, and means for conductively connecting the wound capacitor core and the second interior region. The wound capacitor core is arranged in the first interior region in such a manner that a void is positioned between the wound capacitor core and the side surface. A potting material is disposed in the void, and a capacitor interface is disposed in the second interior region, and in communication with the wound capacitor core via the means for conductively connecting the wound capacitor core and the second interior region.

According to a still further aspect of the present invention, an electronic device includes a housing having a first interior region and a second interior region. The second interior region is sized to receive an electronic interface. The device also includes a wound capacitor core adapted for electrical communication with the second interior region, and a capacitor potting material disposed in contact with the first interior region and the wound capacitor core. The wound capacitor core may be shaped substantially similar to and smaller than said first interior region.

Figure 1A:
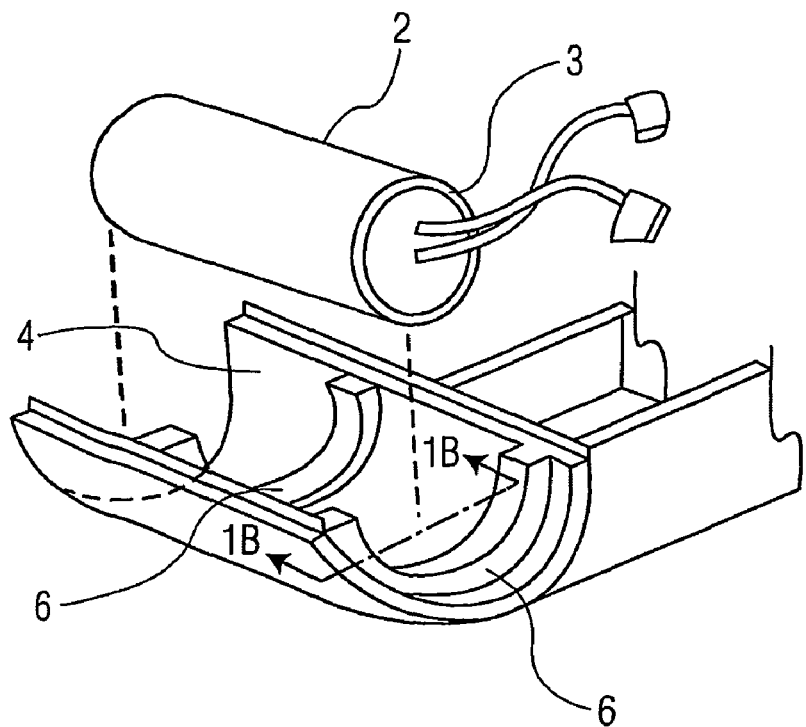
FIG. 1 illustrates an external defibrillator assembly with a prior art capacitor component.
Figure 1B:
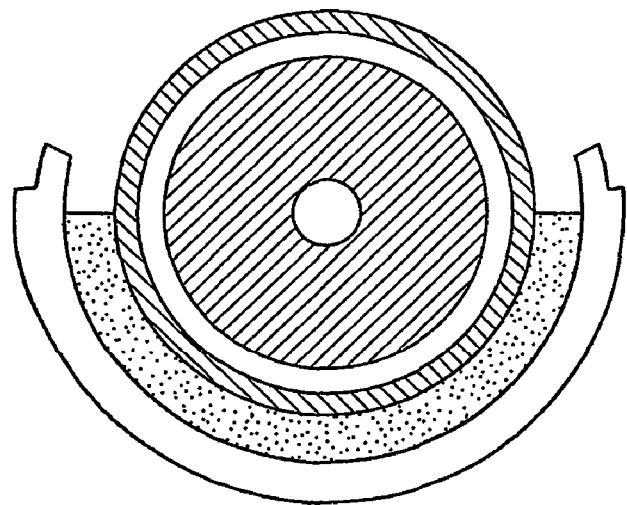
Figure 2:
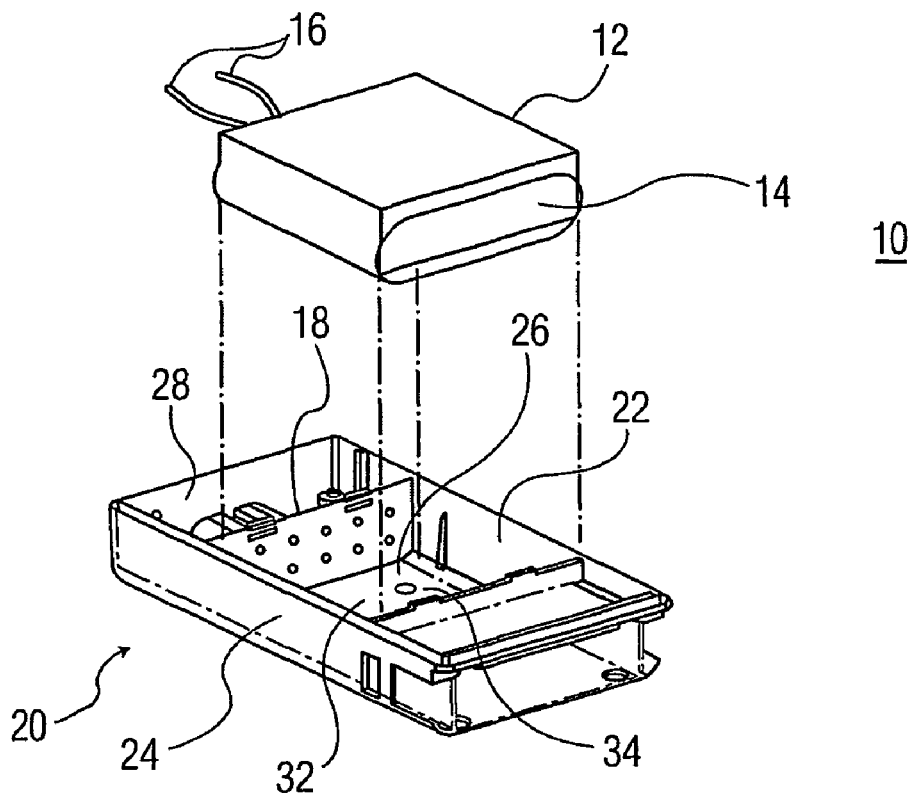
FIGS. 2 and 3 are perspective views of an apparatus for packaging an energy storage capacitor in accordance with certain aspects of the present invention.

Turning now to the drawings, wherein like numerals designate like components, FIG. 2 is an exploded perspective view of an apparatus 10 for packaging an energy storage capacitor 12 in accordance with aspects of the present invention. Energy storage capacitor 12 preferably includes a wound core 14, such as a metallized film core. Wound core 14 has tab terminals 16 extending therefrom, which are preferably directly connectable (for example, by soldering) to capacitor interface electronics 18 (discussed further below). Unlike prior art energy storage capacitors, however, energy storage capacitor 12 forgoes a protective enclosure, such as can 3 surrounding wound core 14. Instead, aspects of the present invention recognize that can 3 is redundant and space-consuming, and instead relies on a housing 20 for protection.

Housing 20 includes an interior surface 22 and an exterior surface 24. Exterior surface 24, which is shown in part, preferably at least in part surrounds interior surface 22 during normal operation of apparatus 10. Interior surface 22 and exterior surface 24 may be made of one or more suitable materials, such as plastic. Surfaces 22, 24 may be integral—a molded plastic housing, for example—or may be composed of a number of assembled parts.

Housing 20 has at least two interior regions. Region 26 and region 28 are shown in FIG. 2. Region 26 has a cavity, and a rectangular box configuration, defined in part by interior surface 22 and a bottom end 32. The top of region 26 is preferably at least partially open, to allow receipt of wound core 14. Region 26 may also have generally tubular configuration, defined, for example, by a circumferential surface that, geometrically, may be a cylindrical configuration or another configuration.

Figure 3:
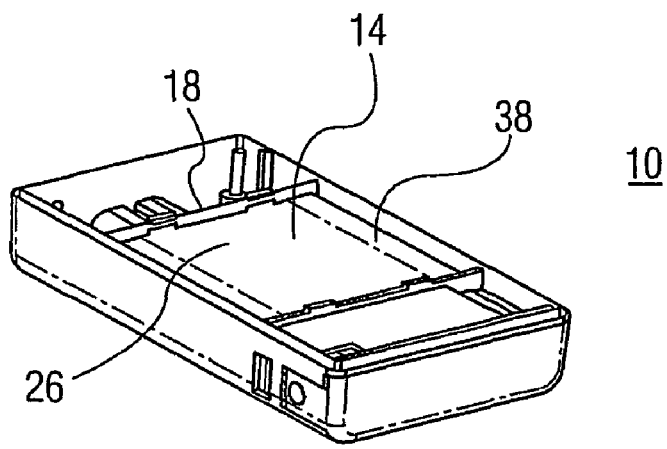

FIG. 3 depicts a perspective view of apparatus 10 with energy storage capacitor 12 installed in accordance with aspects of the present invention. Wound core 14 is disposed in region 26, with tab terminals 16 attached to capacitor interface electronics 18. It is contemplated that any means for conductively connecting wound core 14 and capacitor interface electronics/region 28 may be utilized, including but not limited to leads, pads, or wireless connections, secured to wound core 14 and/or capacitor interface electronics/region 28 in any suitable manner. Substantially any void space remaining between wound core 14 and the walls defining region 26 is filled with a solid capacitor-protecting substance 38, such as an epoxy potting material.

Referring again to FIG. 2, region 28 may be any desirable geometric configuration, and may include one or more compartments. As shown, region 28 is a single, substantially rectangular compartment, which houses capacitor interface electronics 18. Electronics 18 are preferably associated with an external defibrillator, which may be automatic, semi-automatic, or manual, but may be associated with any other type of electronic instrument that utilizes energy storage capacitor 12. One example of electronics 18 is a circuit board.

Housing 20, therefore, may ultimately form packaging for an electronic instrument itself. When capacitor packaging is a part of the electronic instrument in accordance with aspects of the present invention, redundant capacitor housings such as cans are eliminated, and more capacitor volume in the electronic instrument is actually used to store electrical energy—increasing volumetric efficiency. The end result of aspects of the present invention is an electronic instrument that may be made smaller and more rugged, has a decreased need for fasteners and additional wiring leads, and benefits from simplified and/or lower-cost assembly and manufacturing.

Figure 4:
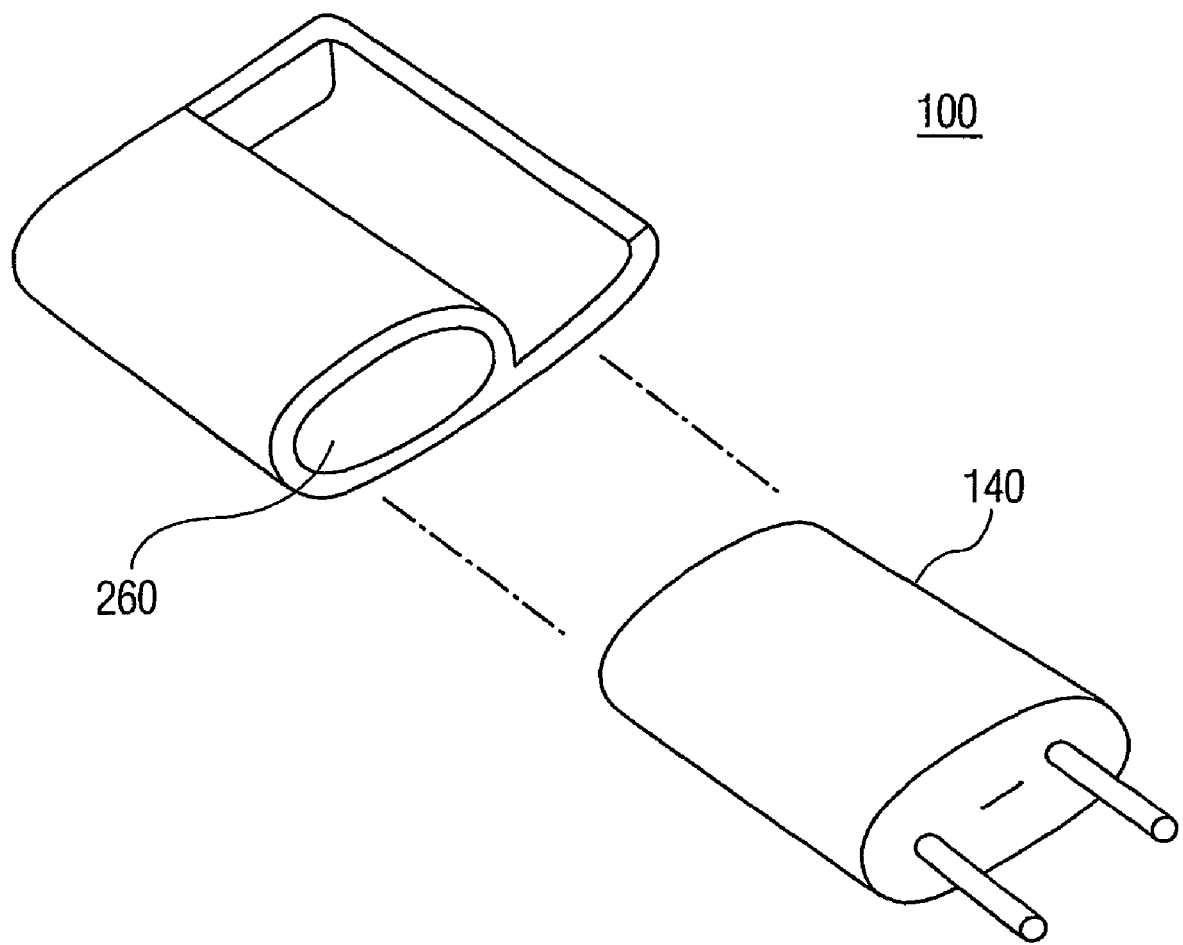
FIG. 4 is perspective view of an apparatus for packaging an energy storage capacitor in accordance with other aspects of the present invention.

Further space utilization efficiencies may be achieved by using alternative geometric configurations to define region 26. An apparatus 100 with a flat-oval configuration is shown in an alternate embodiment of FIG. 4, for example. In this alternate embodiment, wound core 140 is in an oval shape, corresponding to an oval shape of interior region 260. It will be appreciated that a number of geometric configurations of region 26 are possible, and such configurations may depend on the corresponding shape of the wound core 14, or may be independent of the shape of wound core 14.

Figure 5:
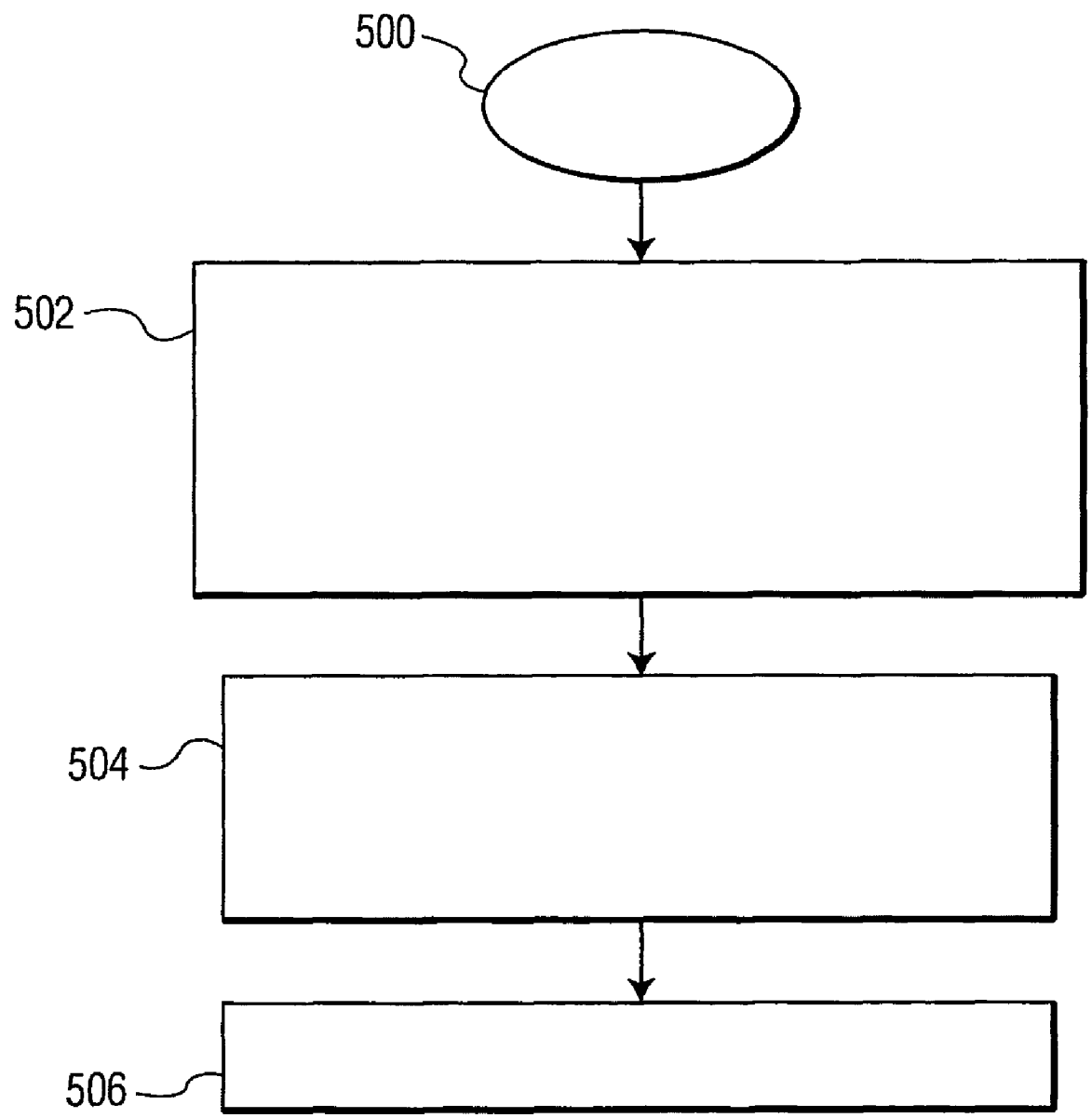
FIG. 5 is a flowchart of a method for packaging an energy storage capacitor in accordance with aspects of the present invention.

As shown in FIG. 5, a flowchart showing a method for packaging an energy storage capacitor, such as capacitor 12, having a wound core (for example, wound core 14) adapted for communication with (for example, via tab terminals 16) capacitor interface electronics, such as electronics 18, associated with an electronic instrument such as an external defibrillator, begins at step 500, and continues at block 502, where an interior housing surface, such as surface 22, is provided. Interior housing surface includes a first region (region 26, for example) and a second region (region 28, for example). The first region has a generally boxlike configuration defined by a side surface, a closed first end, and an at least partially open second end. The first region may be bounded by, for example, surface 22, bottom end 32, and open top end 34. The second region is sized to receive the capacitor interface electronics. At block 504, the wound core is arranged in the first region, so that a void, such as void 36, is positioned between the wound core and the side surface, and the wound core is positioned for communication with the capacitor interface electronics, when the capacitor interface electronics are disposed in the second region. A potting material, such as material 38, is deposited into the void, at step 506. The potting material preferably substantially fills the void, and may be a material like oil or epoxy, such materials being well known and widely available.

The embodiment(s) depicted and described herein are meant to be illustrative in nature, and it will be understood that housings of any shapes and sizes may be designed using the principles set forth herein, and used for various commercial and consumer applications. It will also be understood that aspects of the invention are not limited to the specific embodiments described above, that other and further forms of the invention may be devised without departing from the spirit and scope of the appended claims and their equivalents, and that aspects described and claimed herein are to be accorded the widest scope consistent with the principles and features disclosed herein.

The invention claimed is:

1. An apparatus for packaging an energy storage capacitor in an external defibrillator, the apparatus comprising:
a defibrillator housing having a first interior region and a second interior region;
capacitor interface electronics located in the second interior region;
a wound core disposed in the first region of the housing and adapted for electrical connection to the capacitor interface electronics, the wound core being arranged in such a manner that a void for receiving potting material is positioned between the wound core and a side surface of the housing;
a conductive path adapted to electrically connect the wound core in the first region of the housing to the capacitor interface electronics in the second region of the housing;
the first region being sized to receive the wound core and the potting material, and having a cavity defined by the side surface, a closed first end, and an at least partially open second end, the second region being sized to receive the capacitor interface electronics; and
an exterior housing surface arrangeable to at least in part surround each of the first and second interior regions.

2. The apparatus according to claim 1, further comprising: a potting material substantially filling the void.

3. The apparatus according to claim 2, wherein the potting material comprises one of oil and epoxy.

4. The apparatus according to claim 1, wherein the housing and exterior housing surface comprise a molded plastic housing.

5. The apparatus according to claim 1, wherein the housing and exterior housing surface comprise a plurality of interconnected parts.

6. The apparatus according to claim 1, wherein the capacitor interface electronics comprise a circuit board.

7. The apparatus according to claim 1, wherein the side surface comprises one of an oval surface, a circular surface and a box-like surface.

8. A method for packaging the energy storage capacitor of claim 1, the energy storage capacitor having the wound core adapted for communication with the capacitor interface electronics, the method comprising:
   providing the housing having the first region and the second region, the first region having a cavity defined by the side surface, the closed first end, and the at least partially open second end, the second region sized to receive the capacitor interface electronics;
   arranging the wound core in the first region in such a manner that the void for receiving the potting material is positioned between the wound core and the side surface, and the wound core is positioned for communication with the capacitor interface electronics when the capacitor interface electronics are disposed in the second region; and
   depositing the potting material into the void.

9. The method according to claim 8, further comprising:
   disposing the capacitor interface electronics in the second region; and
   establishing electrical communication between the wound core and the capacitor interface electronics.

10. The method according to claim 8, wherein the capacitor interface electronics comprise a circuit board.

11. The method according to claim 8, wherein the potting material comprises one of oil and epoxy.

12. The method according to claim 8, wherein the housing comprises a molded plastic housing.

13. The method according to claim 8, wherein the housing comprises a plurality of interconnected plastic parts.

14. The method according to claim 8, wherein the side surface comprises one of an oval surface, a circular surface and a box-like surface.

15. An external defibrillator, comprising:
   a housing comprising:
      a first interior region and a second interior region, the first interior region defining a first cavity and having a having a configuration defined by a side surface, a closed first end an at least partially open second end, the second interior region defining a second cavity;
   a wound capacitor core arranged in the first interior region in such a manner that a void is positioned between the wound capacitor core and the side surface;
   an electrical path for conductively connecting the wound capacitor core and the second interior region;
   a potting material disposed in the void;
   a capacitor interface disposed in the second interior region, the capacitor interface in communication with the wound capacitor core via the electrical path; and
   an exterior housing surface arrangeable to at least in part surround each of the first and second interior regions.

* * * * *